United States Patent [19]

Quijano et al.

[11] Patent Number: 5,500,014
[45] Date of Patent: Mar. 19, 1996

[54] BIOLOGICAL VALVULAR PROTHESIS

[75] Inventors: R. C. Quijano, Laguna Hills; Aws Nashef, Huntington Beach; Keith Myers, El Toro, all of Calif.

[73] Assignee: Baxter International Inc., Deerfield, Ill.

[21] Appl. No.: 240,286

[22] Filed: May 9, 1994

Related U.S. Application Data

[63] Continuation of Ser. No. 500,821, Mar. 28, 1990, abandoned, which is a continuation-in-part of Ser. No. 359,449, May 31, 1989, abandoned.

[51] Int. Cl.⁶ .................................................... A61F 2/214
[52] U.S. Cl. .................................... 623/2; 623/1; 623/12; 623/66
[58] Field of Search ............................ 623/1, 2, 11, 12, 623/66

[56] References Cited

U.S. PATENT DOCUMENTS

| | | |
|---|---|---|
| 2,127,903 | 8/1938 | Bowen . |
| 2,453,056 | 11/1948 | Zack . |
| 2,832,078 | 4/1958 | Williams . |
| 3,254,650 | 6/1966 | Collito . |
| 3,254,651 | 6/1966 | Collito . |

(List continued on next page.)

FOREIGN PATENT DOCUMENTS

| | | |
|---|---|---|
| 202031 | 4/1985 | European Pat. Off. . |
| 303767 | 2/1989 | European Pat. Off. . |
| 2657255A | 6/1978 | Germany . |
| 3207690 | 9/1983 | Germany . |

(List continued on next page.)

OTHER PUBLICATIONS

"Experimental Prosthetic Vein Valve", Taheri et al American Journal of Surgery, Vo.. 156, pp. 111–114 (1988).
"Reconstruction of Venous Valves", R. Gottlob & R. May, Venous Valves, 1986, Part V, Section 3.
"Reconstruction of Venous Valves", Venous Valves, R. Gottlob, R. May, Part V, section 3 (Springer–Verlang/Wien, 1986).
"Development of a presosthetic venous valve", Journal of Biomedical Materials Research, Schmidt et al, vol. 19, pp. 827–832 (1985).
"Venous Prosthetic Valves, The First Step Toward an Investigation in the Canine Model", Gerlock, Phifer, McDonald, Investigative Radiology, vol. 1 (1986).
"A technique for correction of truncus arteriosus types I and II without extracardiac conduits", Barbero–Marcial, Atik, Riso, Jatene, Journal of Thoracic and Cardiovascular Surgery, vol. 99, No. 2, Feb. 1990.
"Femoral Venin Valve Incompetence: Treatment with a Xenograft Monocusp Patch", Garcia–Rinaldi, Revuelta, Martinez, Granda, De Santos, Journal of Vascular Surgery, vol. 3, pp. 932–935 (1986).
"Experimental Prosthetic Vein Valve", Taheri, Rigan, Wells, Mentzer, Shores, The American Journal of Surgery, vol. 156, pp. 111–114 (1988).
"Truncus Arteriosus", Cardiac Surgery Morphology, Diagnostic Criteria, Natural History, Techniques, Results and Indications, Kirklin, Barratt–Boyes, (John Wiley & Son) (1986) pp. 911–931).

Primary Examiner—David Isabella
Attorney, Agent, or Firm—Debra D. Condino

[57] ABSTRACT

A biological valvular prosthesis defined by a chemically fixed biological derived conduit having at least one integrally formed tissue valve. The chemical fixation of the valve ensures that the leaflets remain open under normal forward blood flow conditions, but close under minimal backflow pressure. The biological valvular prostheses are useful in the replacement of venous valves and other biological valves. The biological valvular prosthesis may also be in the form of a tubular conduit bearing one tissue valve. This valvular conduit prosthesis is useful for the reconstruction of the pulmonary artery to correct various types of congenital defects.

14 Claims, 7 Drawing Sheets

U.S. PATENT DOCUMENTS

| | | |
|---|---|---|
| 3,736,598 | 6/1973 | Bellhouse et al. . |
| 3,966,401 | 6/1976 | Hancock et al. . |
| 3,974,526 | 8/1976 | Dardik et al. . |
| 3,988,782 | 11/1976 | Dardik et al. . |
| 4,056,854 | 11/1977 | Boretos et al. . |
| 4,086,665 | 5/1978 | Poirier . |
| 4,118,806 | 10/1978 | Porier et al. . |
| 4,247,292 | 1/1981 | Angell . |
| 4,340,977 | 7/1982 | Brownlee et al. . |
| 4,350,492 | 9/1982 | Wright et al. . |
| 4,352,358 | 10/1982 | Angelchik et al. . |
| 4,372,743 | 2/1983 | Lane . |
| 4,451,936 | 6/1984 | Carpentier et al. . |
| 4,466,139 | 8/1984 | Ketharanathan . |
| 4,670,286 | 6/1987 | Nyilas et al. . |
| 4,671,797 | 6/1987 | Vrandecic Pedero . |
| 4,692,164 | 9/1987 | Dzemeshkevich . |
| 4,725,274 | 2/1988 | Lane et al. . |
| 4,728,328 | 3/1988 | Hughes et al. . |
| 4,816,029 | 3/1989 | Penny, III et al. . |
| 4,851,000 | 7/1989 | Gupta . |
| 4,938,740 | 7/1990 | Melbin . |
| 4,957,508 | 9/1990 | Kaneko et al. . |
| 5,089,014 | 2/1992 | Holfert . |
| 5,108,430 | 4/1992 | Ravo . |
| 5,192,289 | 3/1993 | Jessen . |

FOREIGN PATENT DOCUMENTS

| | | |
|---|---|---|
| 2039652 | 11/1979 | United Kingdom . |
| WO81/00668 | 3/1981 | WIPO . |
| WO82/01644 | 5/1982 | WIPO . |
| WO87/04915 | 8/1987 | WIPO . |
| A61F224D | 1/1988 | WIPO . |
| WO88/00459 | 1/1988 | WIPO . |
| WO89/02254 | 3/1989 | WIPO . |
| WO80/01460 | 7/1989 | WIPO . |
| WO90/14804 | 12/1990 | WIPO . |
| WO93/00868 | 1/1993 | WIPO . |

# BIOLOGICAL VALVULAR PROTHESIS

RELATED APPLICATIONS

This is a continuation of application Ser. No. 07/500,821 filed on Mar. 28, 1990 now abandoned, which is a continuation-in-part of U.S. patent application Ser. No. 359,449 filed May 31, 1989 now abandoned.

BACKGROUND OF THE INVENTION

The present invention is directed to biological valvular prosthesis and to methods of making the same. In particular, the present invention is directed to valvular prostheses formed from chemically fixed biological venous valve segments. These valvular prostheses contain one or more venous valves, with each venous valve having two or more leaflets chemically fixed in a position to ensure that the leaflets open under minimal forward blood flow pressures, but close under the application of backflow pressure.

There are different embodiments of the biological valvular prosthesis of the invention, each of which has a different type of application. Generally, the biological valvular prostheses are useful in applications which require the replacement of a valve. For example, one application involves the replacement of a defective or diseased venous valve. In another application the valvular prosthesis is used for correcting truncus arteriosus, a congenital defect where the pulmonary and aortic arteries join to form a single artery having a single valve. In this application the pulmonary and aortic arteries are surgically separated to isolate the blood flow. The valvular prosthesis of the invention is used to route blood from the right ventricle to the pulmonary artery. The integral valve of the valvular prosthesis functions as the semilunar valve normally present at the base of the pulmonary artery.

As stated, one application is the replacement of diseased or damaged venous valves. Venous valves are valves located in the veins. Blood circulated from the arterial to the venous system, with the blood pressure greatest in the arterial system. Blood pressure, as provided by heart activity in the arteries, is normally sufficient to maintain the flow of blood in one direction. The pressure of the blood in the veins is much lower than in the arteries principally due to the distance from the heart. The primary benefit of venous valves is the ability to limit backflow of blood traveling through the venous system. Numerous venous valves are located throughout the veins ensuring that the blood travels through the veins towards the heart.

The normally low blood pressure in the venous system is supplemented by the contraction of skeletal muscles. The contraction of the muscles compresses and drives the blood through the veins. The venous valves check blood flow through the veins, ensuring the drive of the blood towards the heart. Any damage to the venous valves disrupts this normal blood flow.

Venous valves also evenly distribute blood in the veins by segregating portions of blood flowing through the venous system. A further benefit provided by venous valves is checking the backflow of blood through the veins which minimizes or reduces the effect of a sudden increase in blood pressure, e.g. upon heavy exertion.

Venous valves are particularly important in the lower extremities, e.g. legs. The venous system in the lower extremities generally consists of deep veins and superficial veins which lie just below the skin surface. The deep and superficial veins are interconnected by perforating veins. Blood generally flows upwards through the legs towards the heart, and from the superficial to deep veins. The venous valves are situated in the deep, superficial and perforating veins to ensure the direction of blood flow.

Venous valves can become incompetent or damaged by disease, e.g. phlebitis, injury or a result of inherited malformation. Incompetent or damaged valves usually leak blood, even at low blood pressures. These valves fail to prevent the backflow of blood, which is particularly troublesome in the veins of the lower extremities.

The backflow of blood passing through leaking venous valves can cause numerous problems. As previously mentioned, blood normally flows upwards from the lower extremities, and from the superficial to deep veins. Leaking venous valves allow for blood regurgitation reflux causing blood to improperly flow back down through the veins. Blood can then stagnate in sections of certain veins, and in particular the veins in the lower extremities. This stagnation of blood raises blood pressure and dilates the veins and venous valves. The dilation of one vein may disrupt the proper functioning of other venous valves. The dilation of these valves may lead to chronic venous insufficiency. Chronic venous valve insufficiency may lead to skin pigmentation, edema and ulcers. If neglected, chronic valve insufficiency will require bed rest and eventually limb amputation.

Numerous therapies have been suggested to correct incompetent valves. Less invasive procedures include the use of elastic stockings. These procedures are usually inadequate for most conditions. Other procedures involve surgical operations to repair, reconstruct or replace the incompetent or damaged valves. Some investigators have attempted to repair incompetent valves by surgically restricting the valve circumference, such as by suturing the vein to form a tighter closing or restrict dilation of the valve. Other investigators attempted to restrict dilation of the valve by wrapping a stiff cloth about the valve.

Still other surgical procedures include valvuloplasty, transplantation and transposition of veins. Valvuloplasty involves the surgical reconstruction of the valve. Transposition of veins involves surgically bypassing sections of veins possessing the incompetent or damaged valves with veins possessing viable valves. Transplantation involves surgically transplanting one or more of a patient's viable valves for the incompetent or damaged valve. For a more detailed discussion of these techniques see *Venous Valves*, by R. Gottlob and R. May, published by Springer-Verlang/Wien, Part V, section 3. "Reconstruction of Venous Valves", 1986.

The above surgical procedures provide limited results. The leaflets of venous valves are generally thin, and once the valve becomes incompetent or destroyed, any repair provides only marginal relief. Venous valves are usually damaged during handling when the venous valve is being reconstructed, transpositioned or transplanted. The endothelium tissue layer of the vein may also be damaged during handling. This reduces the viability of the vein graft after implant.

Another disadvantage with transplantation procedures is the need to use the patient's own vein segment, otherwise the possibility of rejection arises. The use of a patient's own vein segment predisposes that the incompetence or damage did not arise from inherited factors or diseases which will affect the transplanted valve. For a complete discussion concerning the disadvantages of the discussed surgical procedures see the above referenced portion of *"Venous Valves"*.

The only present alternative to the preceding surgical procedures is removing the valve completely. The removal of an incompetent valve at least prevents an impediment to normal blood flow. The problem associated with backflow is not overcome by the removal of the valve.

Many workers have sought to design a suitable valvular prosthesis. A prosthesis would have to provide a valve which would function similar to a natural valve.

A design of an artificial venous valve prosthesis was reported in "Development of a prosthetic venous valve", Schmidt et al, *Journal of Biomedical Materials Research*, Vol. 19, pages 827–832 (1985). These investigators attempted to prepare artificial venous valves. One type of artificial valve was constructed by molding glutaraldehyde fixed, umbilical cord segments. Specially treated segments were placed over the end of an aluminum rod which had been sculpted into a bicuspid shaped valve. Another type of artificial valve was prepared by dip casting a mandrel in liquid Pellethane polymer. The prepared casting was cut with a scalpel to define the separate valve leaflets. The results of the reported study indicate the necessity of constructing a more reliable artificial venous valve prosthesis.

In another investigation, researchers implanted cardiac prosthetic valves in canines, see "Venous Prosthetic Valves, The First Step Toward an Investigation in the Canine Model", Ami Gerlock M.D., Travis Phifer M.D. and John McDonald M.D., *Investigative Radiology*, Vol. (1986). The purpose of this investigation was to observe the operation of the larger, more rigid cardiac valve in the venous system. This study demonstrated the unsuitability of cardiac valvular prosthesis for transplantation in the venous system.

Xenograft monocusp patches were examined for possible use in repairing incompetent venous valves, see "Femoral Vein Valve Incompetence: Treatment with a Xenograft Monocusp Patch", Raul Garcia-Rinaldi, M.D., Ph.D., J. M. Revuelta, M.D., Ph.D., Manuel Martinez, M.D., Enrique Granda, M.D. and Luis De Santos, M.D., *Journal of Vascular Surgery*, Vol. 3, pages 932–935(1986). While these workers found some success in the implantation of patches, they recognized the advantage of a truly prosthetic device for replacement of incompetent venous valves.

A titanium venous valvular prosthesis has been suggested by Taheri. This valvular prosthesis is discussed more fully in "Experimental Prosthetic Vein Valve", Syde A. Taheri et al, "The American Journal of Surgery, Vol. 156, pages 111–114(1988). The major disadvantage with this type of prosthesis is hemolysis and thrombosis. Damage to the blood as it flows through the valve is enhanced by the small diameter of the valves. Use of such valves requires treatment of the patient with anticoagulants.

Prosthetic heart valves and vascular grafts are commercially available. Such devices may be constructed from artificial and natural materials. Natural tissues used for the construction of prosthetic devices are usually preserved, or fixed in a suitable chemical tanning procedure.

Chemical tanning procedures serve to preserve the tissue to minimize deterioration after implantation, and reduce the possibility of rejection of the device by the host. For example, natural tissues may be treated with a glutaraldehyde solution, with such processes taught in U.S. Pat. No. 4,372,743, issued to Lane on Feb. 8, 1983; and U.S. Pat. No. 3,966,401, issued to Hancock et al on Jun. 29, 1976.

The process taught in Lane involves a low pressure fixation process. This process reduces damage to the valve leaflets during the fixation process. The Hancock et al process involves the alternating pulsation of pressure within the heart valve or vessel.

Examples of prosthetic heart valves constructed at least partially from biological tissue are generally disclosed in U.S. Patent No. 3,736,598, issued to Bellhouse et al on Jun. 5, 1973; U.S. Pat. No. 2,832,078, issued to Williams on Apr. 29, 1958; U.S. Pat. No. 4,451,936, issued to Carpentier et al on Jun. 5, 1984; and U.S. Pat. No. 4,725,274, issued to Lane et al on Feb. 16, 1988.

Prosthetic vascular grafts are also known. Examples of vascular grafts or blood vessels prepared from artificial materials are disclosed in U.S. Patent Nos. 4,086,665, issued to Poirier on May 2, 1978; U.S. Pat. No 4,118,806, issued to Poirier on Oct. 10, 1978; and U.S. Pat. No. 4,670,286, issued to Nyilas et al on Jun. 2, 1987. The artificial blood vessels taught in the Poirier references may include porcine xenograft valves. The inclusion of the valve is required when the artificial blood vessel bypasses a natural heart valve. The main disadvantage with using the vascular graft containing a procine xenograft valve, as described in the Poirier references, is the development of luminal deposits of fibrinous material after a period of time. The development results from the synthetic grafts positioned on either side of the valve.

Vascular grafts may also be prepared from natural tissues. Such grafts are prepared by chemically treating segments of biografts. Examples of these grafts are disclosed in U.S. Pat. No. 4,671,797, issued to Vrandecic Pedero on Jun. 9, 1987 and U.S. Pat. No. 4,466,139, issued to Ketharanathan on Aug. 21, 1984. Hancock et al also discloses the preparation of veins and arteries.

While bioprosthetic heart valves and vascular grafts are known, bioprosthetic venous valves are presently not available. The major deterrent in constructing venous valves is the need to provide a valve which remains normally open, but closes under slight backflow. Another deterrent in constructing such valves is the need to provide proper valve leaflet and sinus geometry as the valve opens and closes. Prosthetic heart valves, and the methods of preparing the same, are not suitable as venous valve replacements. The unsuitability of using prosthetic cardiac valves as replacements for venous valves was discussed in the article by Gerlock et al. Prosthetic heart valves are usually made from porcine valves. Porcine heart valves have a geometry unsuitable as a replacement for venous valves. These types of valves are also generally larger than venous valves, and include valve leaflets generally thicker and stiffer than the leaflets of venous valves. The thicker heart valve leaflets require a greater opening pressure. The greater required opening pressure makes such valves unsuitable for the venous system.

The techniques used to prepare prosthetic heart valves make the resulting prosthesis more unsuitable for use as a venous valve replacement. As stated, venous valve leaflets are thinner and must remain open under normal venous flow conditions. The techniques used to prepare cardiac valvular prosthesis fix the leaflets to remain normally closed, and to open only upon the exertion of relatively higher pressures. These tanning techniques also form stiffer leaflets which further require greater pressures to open the valve.

This same rationale is also applicable to those procedures used for preparing vascular prothesis. The utilized tanning processes would not provide the valve leaflets with the ability to remain open during normal venous blood flow and close upon the occurrence of backflow. In fact, the patent to Vrandecic Pedero specifically requires the removal of any valves present in the arterial biograft used to prepare the vascular prosthesis.

It would thus remain desirable to provide a biological venous valvular prosthesis having leaflets which remain open under normal flow conditions, but close upon a minimal backflow.

A further application for the valvular prosthesis of the invention is in the treatment of congenital defects of the right ventricular outflow tract. For example, a valvular prosthesis in the form of a tubular member bearing at least one venous valve may be used to bypass a defective semilunar valve of the pulmonary artery, or even a defective pulmonary artery. Examples of defects of the right ventricular outflow tract are truncus arteriosus, pulmonary atresia and pulmonary stenosis.

Truncus arteriosus is a congenital cardiovascular malformation where a single artery, formed by the joining of the pulmonary and aortic arteries, arises from the heart. This single artery typically bridges the right and left ventricles. This congenital defect may al so be accompanied by a ventricular septal defect, which is a hole through the heart wall between the right and left ventricles.

While the mortality from this defect is high, attempts are usually made to repair the defect. This involves surgically separating the pulmonary segment from the aortic segment, and sealing the resulting opening of the aortic artery. If present, the ventricular septal defect is repaired by suturing the opening closed or suturing a patch over the opening. The pulmonary artery is then reconstructed by various techniques, which usually require the construction or insertion of a valve.

One technique utilizes a homograft which is surgically interposed in a graft sutured between the right ventricle and the pulmonary artery. For a more detailed discussion of this technique see "Truncus Arteriosus", Chapter 28 of *CARDIAC SURGERY Morphology, Diagnostic Criteria, Natural History, Techniques, Results, and Indications*, by John W. Kirklin, M.D. and Brian G. Barratt-Boyes, KBE, MB, ChM, Published by John Wiley & Sons (1986).

Another surgical procedure involves the construction of a bypass from the right ventricle to the pulmonary artery segment using a pericardial tissue patch. A pericardial monocusp is formed in the bypass. This procedure is discussed in more detail in "A technique for correction of truncus arteriosus types I and II without extracardiac conduits", by Barbero-Marcial M.D., Riso M.D., Atik M.D. and Jatene M.D., *Journal of Thoracic and Cardiovascular Surgery*, Vol. 99, Number 2, Feb. 1990.

A major disadvantage to the above discussed surgical procedures for the repair of truncus arteriosus is the use of multiple components in the reconstruction of the various arteries from the single large artery. That is, the first described procedure requires the use of a homograft and vascular graft, typically constructed from polytetrafluoroethylene, while the second procedure requires the use of a pericardial patch and a pericardial monocuspid. These procedures require extensive surgical implantation time, and provide sites for hemolysis.

While these discussed surgical procedures provide some relief from this debilitating congenital defect, improvements in the surgical techniques and prosthesis are necessary.

SUMMARY OF THE INVENTION

The present invention overcomes the above discussed disadvantages by providing a biological valvular prosthesis formed from a biologically derived conduit having at least one tissue valve with leaflets prepositioned to open under normal forward blood flow conditions, but close under minimal backflow pressure, while maintaining the natural geometry of the valve.

The biological valvular prosthesis is formed from a harvested vein segment including one or more venous valves which is chemically fixed to ensure that the leaflets remain open under minimal forward blood flow, while closing under minimal backflow. Generally, the venous valves are chemically fixed with the valve leaflets retained in either the open or closed position. It has been found that in order to ensure a normal opening of the valve leaflets, that the fixation be performed while the leaflets are preferably retained in a substantially open position. The chemical fixation is also performed to ensure that the valve leaflets remain substantially supple so as to close upon minimal backflow pressure.

Specifically, the biological valvular prosthesis and method of preparing the same provides substantially supple valve leaflets that remain substantially open during normal forward blood flow. Generally these flow rates are at least from about 100 milliliters per minute (ml/m), preferably from about 250 to about 550 ml/m, but will close under a minimum backflow pressure, generally a pressure of at least 0.1 millimeters of Mercury (mm Hg).

The precise configuration of the valvular prosthesis of the invention is dependent upon the desired application. The harvested venous valve segment includes the individual valves situated in a vein segment. When the valvular prosthesis is designed to replace a patient's venous valve, the vein segments are cut back at each side of the valve to within a few centimeters of the valve. The resulting prosthesis is a fixed venous valve having only a sufficient amount of the vein segment retained at opposite sides to provide a suture site. The precise length of the retained segments should only be sufficient to minimize the potential of suturing the leaflets during the implantation. The implantation of this valvular prosthesis involves curing the vein into two portions and inserting this prosthesisis between these portions.

Another embodiment useful for replacing a patient's venous valve involves removing the valve sinus regions. This prosthesis is surgically sutured into the patient's vein. This embodiment utilizes a portion of the patient's vein to function as the sinus.

In another application the segments at both sides of the valve are retained to form a tubular prosthesis having one or more valves. The valvular prosthesis of this embodiment may be used to bypass a defective venous valve or replace a defective heart valve. A particularly advantageous use of this tubular prosthesis is in the reconstruction of the pulmonary artery to correct various types of congenital heart defects. The biological valvular conduit prosthesis may be reinforced about the extended vein segments to prevent collapse of such segments. The ends of this conduit may be provided with sewing rings, or other means to facilitate suturing.

One particular congenital heart defect for which the tubular conduit valvular prosthesis may be used is in the correction of truncus arteriosus. One of the vein segments is modified by cutting the segment lengthwise to form a flap-like extension. During the reconstruction of the pulmonary segment of the single artery, this flap portion is sutured about an incision made in the heart wall of the right ventricle, with the opposite end of the valvular conduit sutured to the pulmonary segment which was isolated from the aortic segment.

DESCRIPTION OF THE DRAWINGS

The present invention may be better understood and the advantages will become apparent to those skilled in the art by reference to the accompanying drawings; wherein like reference numerals refer to like elements in the several figures, and wherein.

DESCRIPTION OF THE PREFERRED EMBODIMENTS

The present invention concerns biological valvular prostheses and methods of making the same. The valvular prosthesis has use in various applications, e.g. the replacement of venous valves or the repair of the congenital defect truncus arteriosus. In general, the valvular prosthesis of the invention is constructed by chemically fixing a vein segment containing one or more venous valves. The source of the vein segment may be equines, bovines, caprines or ovines.

The valvular prosthesis of the invention has many applications. The exact configuration of the prosthesis will depend upon the desired application. In particular, the vein segment at either side of the venous valve may either be retained or excised depending upon the final application. The various applications for the valvular prosthesis of the invention requires that the valve leaflets be fixed to remain substantially open under normal blood flow, but close under minimal backflow. This is particularly important when the valvular prosthesis of the invention is used as a venous valve replacement.

Unlike cardiac valves, venous valves normally remain open, and close upon the exertion of any backflow pressure. This distinction between cardiac and venous valves requires a different type of valve and different preparation procedures.

The valvular prosthesis of the invention are prepared with leaflets prepositioned to remain open under normal forward blood flow and close under backflow pressure. By "normal forward blood flow" it is meant that level of blood flow through the particular vein. Blood flow rates vary between different veins, but generally will be greater than at least about one hundred milliliters/minute.

By "backflow" it is meant the direction away from the normal forward blood flow, and in particular the flow direction away from the heart or away from the deep veins. Generally, the necessary backflow to close the valves will provide a pressure of at least 0.1 mm Hg.

The valvular prosthesis of the invention will remain substantially open under normal forward blood flow. Typically, the valves will remain greater than about 70 percent open, preferably greater than about 80 to 90 percent open under normal forward blood flow.

The valvular prosthesis of the invention is prepared from harvested vein segments containing one or more venous valves. Preferable vein segments are jugular veins from equines, bovines, caprines and ovines. The vein segments used for the purpose of the invention may have one or more intact valves. A harvested segment having more than one valve may be subdivided for the preparation of one or more venous valvular prosthesis.

After being harvested, any extraneous material, e.g. muscle and fatty deposits and tissue is removed from about the vein. A minimal amount of the segment remains extending out from either side of the valve. The precise length of the segment which extends out from both si des of the valve is dependent upon the particular application for the prosthesis. In certain applications only a few centimeters of the segment will be retained, while for another application the retained segments are longer.

The harvested and cleaned blood vessel and valve is then subjected to a chemical tanning process. Tanning is a well known process involving the treatment of the vessel with an aldehyde solution or other suitable fixative, typically a solution of glutaraldehyde in pH balanced electrolyte buffer. It has been found that the concentration of glutaraldehyde should be from about 0.025 percent to about 0.626 percent of the tanning solution to prepare the supple valve leaflets of the invention. For a more detailed discussion of tanning processes, see the discussion of tissue tanning procedures in *Tissue Valves*, Ed. Marion Ionescu, Chapter 15, by Aubry Woodruff, which reference is incorporated herein by reference.

The valvular prosthesis will now be described with reference to FIGS. 1–6 illustrating the valvular prosthesis as configured as a venous valvular replacement prosthesis, as seen generally at 10. Venous valvular replacement prosthesis 10 is a harvested tubular blood vessel 12 containing at least one intact venous valve, seen generally at 14. Valve 14 may be of the bileaflet or trileaflet type, with the typical type being bileaflet.

Figure 1:
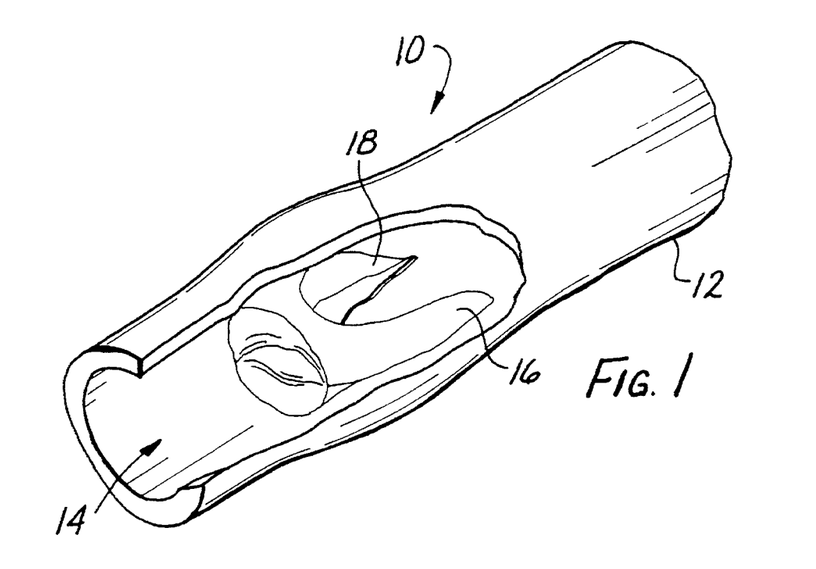
FIG. 1 is a partial section prospective view of a venous valvular replacement prosthesis in accordance with an embodiment of the invention.

The illustrated venous valvular replacement prosthesis 10 contains a single bileaflet valve 14. The original blood vessel segment from which the prosthesis 10 was formed may have included more than one venous valve. However, for this embodiment the original blood vessel segment is cut into individual segments containing separate venous valves. It should be noted that in other embodiments the prosthesis is formed by retaining the multiple valves in a single conduit.

As previously described the venous valvular replacement prosthesis 10 includes a single bileaflet valve 14. This bileaflet valve 14 includes two leaflets, seen at 16 and 18 respectively.

Figure 2:
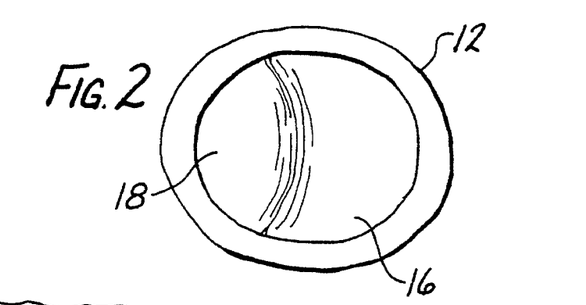
FIG. 2 is an end on view of the venous valvular replacement prosthesis of FIG. 1 viewing the leaflets in a closed position.

As with natural valves, the valve leaflets 16 and 18 are positioned to slightly overlap when the valve is closed, as better seen in FIG. 2. The venous valvular replacement prosthesis 10 is prepared to minimize any interference with this natural overlapping relationship.

As stated, the venous valvular replacement prosthesis 10 is prepared to ensure that the bileaflet valve 14 remains substantially open during normal forward blood flow through the prosthesis 10. The valve leaflets 16 and 18 also remain substantially supple to promote closure of the bileaflet valve 14 under any backflow pressure, generally backflow pressures in excess of 0.1 mm Hg.

That is, the venous valvular replacement prosthesis 10 of the invention is formed to allow the leaflets 16 and 18 to remain supple enough to close under the minimal application of backflow pressure while remaining open during normal forward blood flow. These characteristics allow the venous valvular replacement prosthesis 10 to generally mimic the functioning of natural venous valves.

In accordance with the preferred embodiment of the invention, the process by which the venous valvular replacement prosthesis 10 is prepared prepositions the valve leaflets 16 and 18 in a substantially open position. The fixing of the leaflets 16 and 18 in a substantially open position ensures that the valve will remain substantially open, that is at least 70 percent open during forward blood flow.

In accordance with other, less preferred embodiments, the leaflets 16 and 18 are fixed in either a closed or partially open position. While the resulting prosthesis remains open under normal forward blood flow, the leaflets do not open to as great a degree as when the leaflets 16 and 18 are fixed in an open position.

As stated, the preferred embodiment fixes the valve leaflets 16 and 18 in a substantially open position. The chemical fixing of the valve leaflets 16 and 18 in a substantially open position is provided by subjecting the harvested and cleaned blood vessel containing the venous valve to a tanning process while maintaining a substantially constant flow of tanning fluid, that is the aldehyde solution, through the blood vessel. The leaflets 16 and 18 may also be chemically fixed while retained in a partially open position. The extent to which the valve leaflets are open is controlled by varying the flow rate of the tanning solution through the blood vessel during the fixation process. The resulting prosthesis will have the leaflets fixed anywhere from completely open to about 10 to 70 percent of the normal open position of the valve.

Generally, the process by which the blood vessel containing the venous valve is treated to prepare the venous valvular replacement prosthesis 10 is similar to those tanning procedures used to prepare cardiac heart valves. One specific process is disclosed in U.S. Pat. No. 4,372,743, with the description of the general process for treating animal tissue by the use of aldehyde, and specifically glutaraldehyde being incorporated herein by reference.

A tanning procedure useful for preparing the venous valvular replacement prosthesis 10 in accordance with the preferred embodiment of the invention will be described with reference to FIG. 7. A blood vessel containing one or more venous valves is harvested from a subject animal. Preferably, the blood vessel is a bovine, equine, caprine or ovine external or internal jugular vein.

The harvested blood vessel may contain more than one venous valve. For example, the bovine internal or external jugular veins includes about 2 valves per vein segment. To prepare the venous valvular replacement prosthesis 10 the blood vessel is cleaned and divided into segments containing single valves. The size of the vein segments at both sides of the valve is reduced. As stated, the length of the blood vessel on either side of the valve will be less than about 0.5 cm, preferably about 1 cm to about 3 cm from valve aggar, and about 1 cm to about 2 cm from the valve commissures. The harvested blood vessel is then cleaned and if desired stored in a balanced physiological electrolyte solution for less than 24 hours prior to being subjected to the chemical tanning process.

Figure 7:
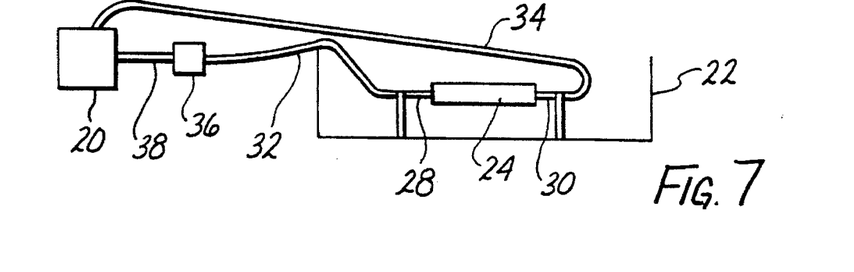
FIG. 7 is a schematic illustration of the apparatus arrangement for preparing a biological valvular prosthesis in accordance with an embodiment of the invention.

The tanning apparatus useful for preparing the valvular prosthesis of the invention is seen generally in FIG. 7. This apparatus includes two fluid tanks 20 and 22. The first fluid tank 20 will contain the tanning solution which will be circulated through the blood vessel. The blood vessel, seen generally at 24, will be held within the second fluid tank 22. The second fluid tank 22 will be filled with additional tanning solution. The blood vessel 24 is mounted upon a support, seen generally at 26. Support 26 includes two opposing stoppers 28 and 30. Each of the stoppers 28 and 30 is formed to fit snuggly within an end of the blood vessel 24.

The stoppers 28 and 30 are also formed with passageways, not shown, which traverse through each of the individual stoppers 28 and 30. The stoppers 28 and 30 are further formed to allow individual pieces of tubing, seen generally at 32 and 34 to be coupled together. Tubing 32 is also connected to a pumping mechanism seen generally at 36. This pumping mechanism 36 may be any suitable type of device which can pump fluid through a tubing. For example, pumping mechanism 36 may be a magnetic-driven centrifugal pump or master flex pump.

Tubing 34 is coupled at its other end to the first fluid tank 20. A third piece of tubing, seen generally at 38, is coupled between the first fluid tank 20 and pumping mechanism 36. The combination of the first fluid tank 20, pumping mechanism 36 and tubing 32, 34 and 38 form a continuous, uninterrupted fluid pathway when the blood vessel 24 is connected to the support 26.

Both the first fluid tank 20 and second fluid tank 22 are filled with a tanning solution. Generally this tanning solution is an aldehyde solution containing from about 0.10 percent to about 1.0 percent of an aldehyde, with the remaining solution being a pH balanced physiological electrolyte solution. Preferably the aldehyde is glutaraldehyde. Other suitable tanning solutions include acrolein or polyepoxy compounds.

The tanning solution in the second fluid tank 22 is maintained at atmospheric pressure. However, if desired, this tanning solution can be placed under pressure by sealing the second fluid tank 22 and circulating the fluid within the second fluid tank 22, or circulating the fluid between the second fluid tank 22 and another tank, not shown.

The rate at which the tanning fluid is circulated through the blood vessel 24 is dependent upon the extent to which the leaflets are to be prepositioned in an open state. This prepositioning ensures that the valve leaflets 16 and 18 will remain open during normal forward blood flow through the venous valvular replacement prosthesis 10. Depending upon the flow rate of the tanning fluid, the valve leaflets 16 and 18 will be prepositioned to greater than about 70 percent of their open position, preferably greater than about 80 to 90 percent.

A further requirement for the tanning process is to provide that the valve leaflets 16 and 18 will remain substantially supple. This suppleness allows the valve leaflets 16 and 18 to close under a minimal backflow. This suppleness is achieved by controlling the concentration of the glutaraldehyde in the tanning solution and the amount of time the blood vessel is subjected to the tanning solution. It has been determined that the concentration of aldehyde in the tanning solution, and the amount of time to which the tissue is subjected to the tanning solution affects the stiffness of the tissue. The aldehyde concentration and tanning time also controls the degree of the bio burden reduction. That is, the bio burden or bacterial growth on the tissue must be reduced below an acceptable level. This level is controlled by the amount of time to which the tissue is subjected to the tanning process.

As stated, the concentration of the aldehyde, i.e. glutaraldehyde, in the tanning solution should be from about 0.025 percent to about 0.626 percent of the tanning solution to prepare the supple valve leaflets of the invention. Preferably, the glutaraldehyde should be about 0.15 percent of the tanning solution to ensure proper suppleness of the leaflet.

The tanning solution within the first fluid tank 20 is circulated through the blood vessel 24 at a rate of from about 0.5 liters/minute (l/m) to about 4 l/m. Preferably the fluid is circulated at a rate of from about 1 l/m to about 3 l/m. The extent to which the leaflets 16 and 18 are fixed in an open position is dependent upon the pressure applied to the leaflets 16 and 18 during the tanning process. For the purposes of describing the invention, the applied pressure is the measured pressure differential across the valve. This pressure differential is measured by taking the difference of the fluid pressure entering over the fluid pressure exiting the blood vessel during the tanning process.

The amount of time in which the blood vessel 24 is subjected to the tanning procedure will also effect the extent to which the valve leaflets 16 and 18 close. The blood vessel 24 is subjected to the tanning process for a sufficient amount of time to attain the desired bio burden and provide for fixed leaflets that remain substantially open under normal forward blood flow while closing under the application of backflow pressure. The exact time is dependent upon the nature of the tissue forming the leaflets and degree of bio burden present on the tissue. Generally, the tanning procedure lasts from about thirty minutes to about four hours, preferably from about two to three hours, and more preferably about three hours.

While the best results are achieved by fixing the valve leaflets in a substantially open position, for certain applications it may be suitable to fix the valve leaflets in a closed position. Fixing the leaflets in the closed position is performed by reversing the flow of the tanning solution through the blood vessel and maintaining a minimal pressure against the valve leaflets. Typically, the pressure applied against the closed leaflets should be around about 0.1 mm Hg.

Figure 3A:
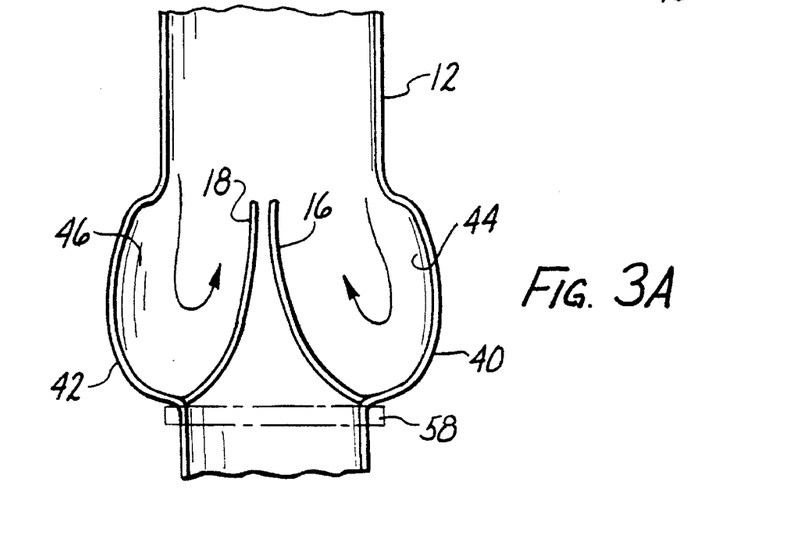
FIG. 3A is a cross-section view of the venous valvular replacement prosthesis of FIG. 1 with the leaflets in the closed position.
Figure 3B:
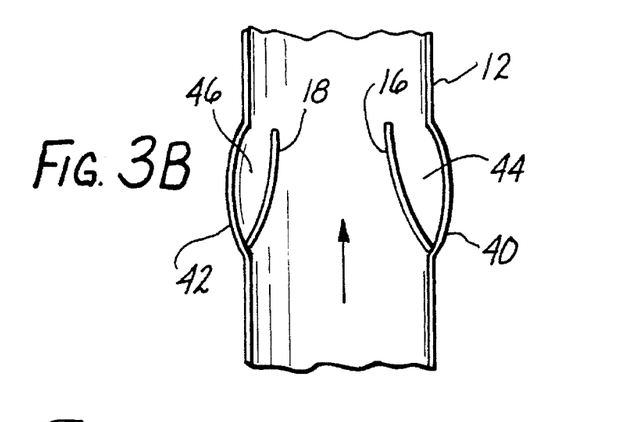
FIG. 3B is a cross-section view of the venous valvular replacement prosthesis of FIG. 1 with the leaflets in the open position.

The operation of the venous valvular replacement prosthesis 10 will now be described with reference to FIGS. 3A and 3B. FIGS. 3A and 3B are schematic illustrations of a venous valvular replacement prosthesis 10. FIG. 3A illustrates a venous valvular replacement prosthesis 10 with the valve leaflets 16 and 18 moving into a closed position. FIG. 3B illustrates a venous valvular prosthesis with the valve leaflets 16 and 18 in a substantially open position.

Associated with each of the valve leaflets 16 and 18 is a sinus, seen respectively at 40 and 42. Each sinus 40 and 42 is generally bulbous in shape and defines a sinus cavity 44 and 46 respectively. With blood flowing in a normal direction through the venous valvular replacement prosthesis 10, as seen in FIG. 3B, the sinus cavity 44 and 46 remain substantially empty of blood with the sinus 40 and 42 being somewhat flat. As blood backs up in the vein in which the venous valvular replacement prosthesis 10 is sutured, the sinus cavity 44 and 46 begin to fill with blood. The filling of the sinus cavity 44 and 46 causes the associated sinus 40 and 42 to bulge outward from the venous valvular replacement prosthesis 10 and begins to force the individual valve leaflets 16 and 18 into a closing position.

Figures 4, 5:
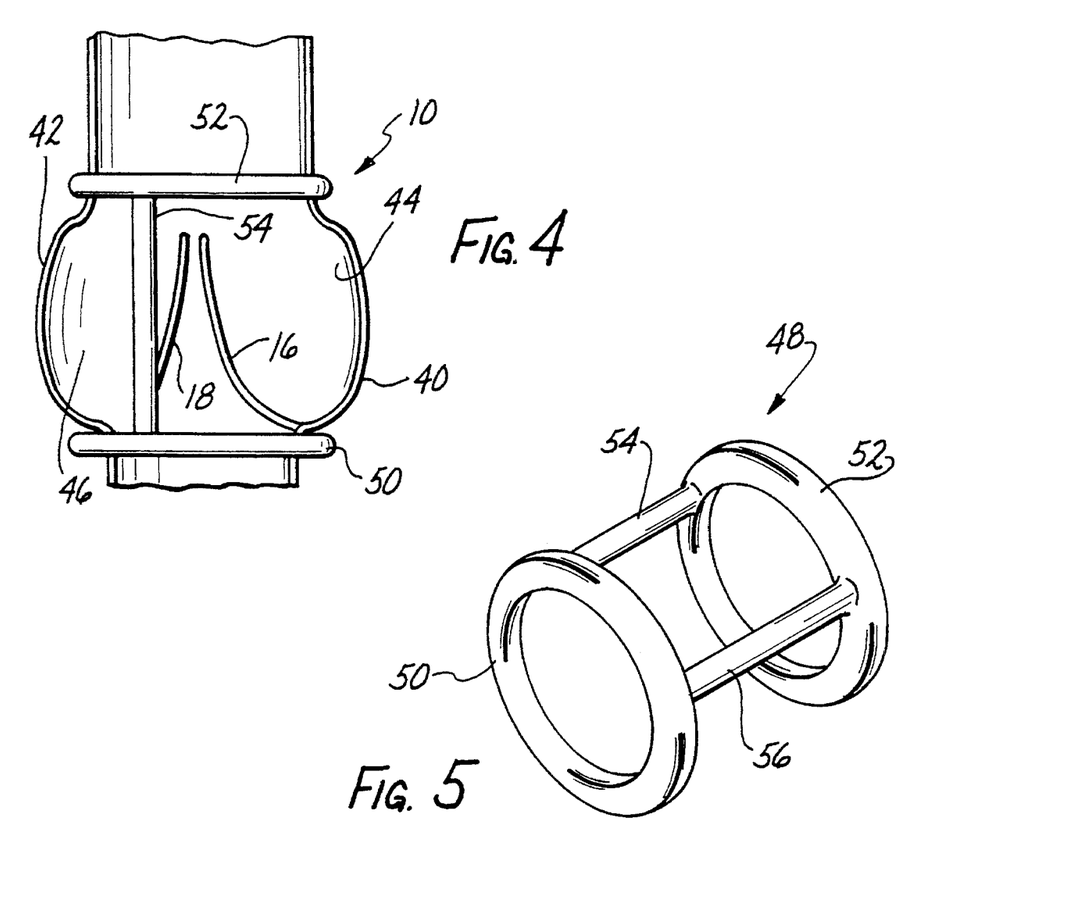
FIG. 4 is a cross-sectional view of a venous valvular replacement prosthesis with a support cage positioned about the segment.
FIG. 5 is a prospective view of a support.

In accordance with a preferred embodiment of the invention, the venous valvular replacement prosthesis 10 is further provided with a supporting cage. One embodiment of this supporting cage is generally seen in FIG. 5 at 48. Cage 48 will be positioned around the exterior of the venous valvular replacement prosthesis 10. The supporting cage 48 functions to control the dilation of the bileaflet valve 14 during pressure increases with the associated blood vessel. The proper positioning of the supporting cage 48 minimizes the dilation of the bileaflet valve 14 and the possible incompetence of the venous valvular replacement prosthesis 10.

The construction of the supporting cage 48 is designed to not interfere with the normal operation of the venous valvular replacement prosthesis 10. In this regard the supporting cage 48 is designed not to restrict the normal filling of the sinus cavity 44 and 46. However, if the pressure within the associated blood vessel and venous valvular replacement prosthesis 10 significantly increases, the supporting cage 48 will restrict further expansion of the sinus cavity 44 and 46. This will limit the extent to which the bileaflet valve 14 dilates and prevent the bileaflet valve 14 from becoming incompetent.

The supporting cage 48 is formed from two circular collars 50 and 52 which are linked by struts 54 and 56. The collar 50 will be positioned about the venous valvular replacement prosthesis 10 at the upstream side of the bileaflet valve 14, while the collar 52 will be positioned at the downstream side. As seen in FIGS. 3A and 3B the diameter of the side of the venous valvular replacement prosthesis 10 upstream from the bileaflet valve 14 is smaller than the diameter of the downstream side. In order to ensure a proper fit, the collar 50 is smaller than collar 52. The individual collars 50 and 52 are dimensioned to provide for a snug fit about the corresponding location of the venous valvular replacement prosthesis 10.

The positioning of the struts 54 and 56 is also critical. As seen in FIG. 2 the valve leaflets 16 and 18 are different sizes. The associated sinus cavity 44 and 46 are of similar size differences. The struts 54 and 56 are fixed between the collars 50 and 52 so as not to interfere with the filling of the sinus cavity 44 and 46.

Figure 6:
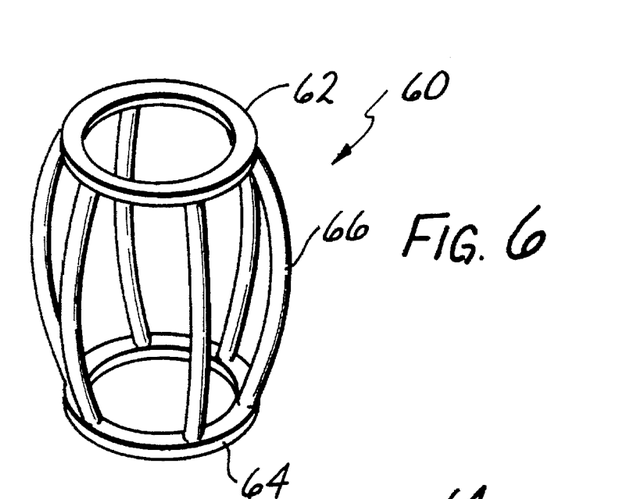
FIG. 6 is a prospective view of another type of support cage.

Referring to FIG. 6, another embodiment of a supporting cage is seen generally at 60. Cage 60 includes two collars 62 and 64 similar in size and positioning as collars 50 and 52 for cage 48. The main difference between cages 48 and 60 is that cage 60 includes a plurality of outwardly bowed ribs or struts, one of which is seen at 66. The number of struts 66 may vary from 4 to 6 equidistantly positioned about the circumference of the cage 60.

Figure 6A:
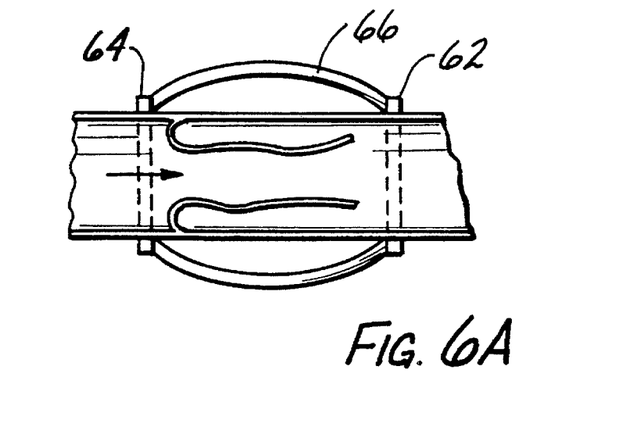
FIGS. 6A and 6B are partially sectioned views of a venous valvular replacement prothesis incorporating the support cage of FIG. 6.
Figure 6B:
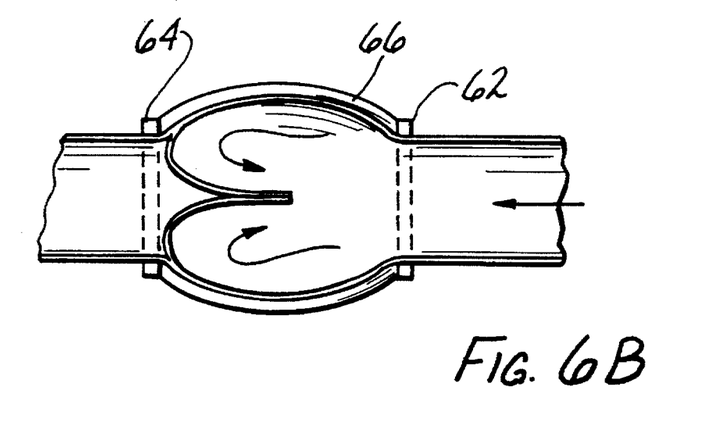

The struts 66 are formed with a sufficient enough outward curvature to allow for the expansion of the sinus during backflow, as better seen in FIG. 6B. The curvature of the struts 66 will not interfere with the operation of the valve during normal forward blood flow as seen best in FIG. 6A.

In accordance with a still further embodiment a single upstream collar may be used in place of the supporting cage 48. This single upstream collar is seen in phantom at 58 in FIG. 3A. The positioning of the collar 58 at the upstream position restrains the dilation of the venous valvular replacement prosthesis 10. If the venous valvular replacement prosthesis 10 restrained downstream from the bileaflet valve 14, the valve 14 could still dilate.

Figure 10:
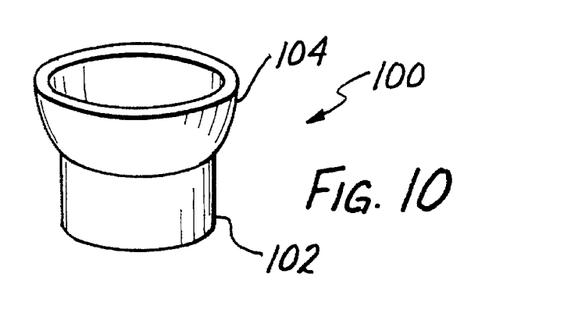
FIG. 10 is a side view of another type of support cage.
Figure 11:
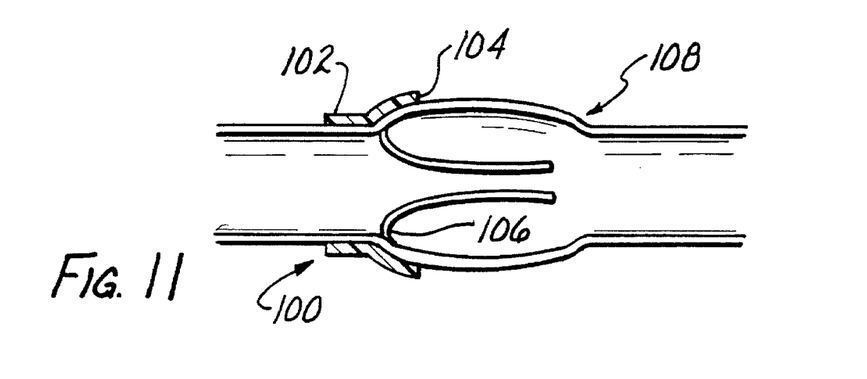
FIG. 11 is a partially sectioned view of a venous valvular replacement prosthesis incorporating the support cage of FIG. 10.

Another embodiment of a support cage is seen in FIG. 10 at 100. This support cage 100 is a generally tubular structure having a first cylindrical section 102 out from which extends an outwardly flaring section 104. This outwardly flaring section 104 is shaped to conform to the outer configuration of the valves sinus. The cylindrical section is juxtapositioned to the venous valve aggar seen generally at 106, with the outwardly flaring section 104 surrounding that portion of the venous valve extending upward from the aggar 106, as better seen in FIG. 11 at 108.

Figure 8:
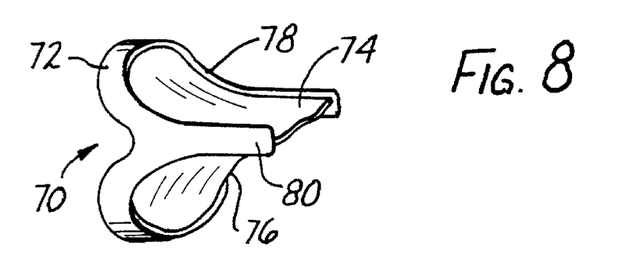
FIG. 8 is a prospective view of a venous valvular replacement prosthesis in accordance with another embodiment of the invention.
Figure 9:
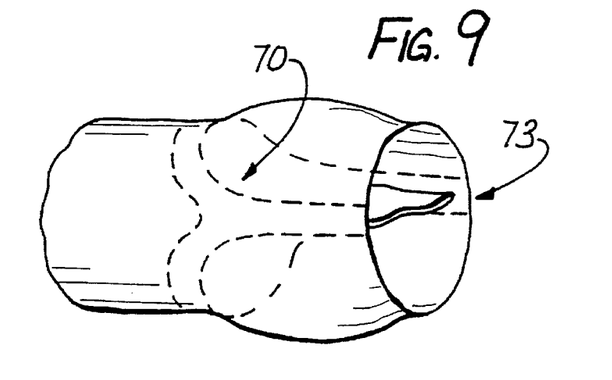
FIG. 9 is a prospective view of a vein incorporating the prosthesis of FIG. 8.

A still further embodiment of the invention is a modification of the venous valvular prosthesis. This modification, which is seen in FIGS. 8 and 9, involves removing the tissue defining the valve sinus areas. The tissue is removed only for the sinus area leaving intact the valve commissures and leaflets. The resulting structure is seen more generally in FIG. 8 at 70. The valvular prosthesis 70 includes the aggar portion of the valve with a small portion of the blood vessel tube extending out therefrom, as seen at 72. The prosthesis 70 also includes the intact leaflets 74 and 76, as well as the commissures 78 and 80. A small portion of the vein wall juxtapositioned the commissures remains intact as seen generally at 79 and 81.

A further modification of this embodiment involves excising a single valve leaflet and a small portion of the vein wall to form a monocuspid prosthesis. This monocusp may then be surgically implanted in a venous valve which possess a single damaged or diseased leaflet.

FIG. 9 illustrates the prosthesis 70 of FIG. 8 as sutured into a vein lumen 73. The described monocuspid may be substituted for the prosthesis 70 where only a single leaflet is damaged or diseased.

The valvular prosthesis of the invention may also be configured to form a valvular conduit prosthesis containing one or more valves. This embodiment of the invention involves retaining a portion of the vein segment at both sides of the valve. One embodiment of the valvular conduit prosthesis is seen generally at 110 in FIGS. 12 and 13. The valvular conduit prosthesis 110 includes a biological vein segment 112 which is chemically fixed as discussed above. The difference between the process of preparing this valvular conduit 110 and the prosthesis 10 described above is the retention of portions 114 and 116 of the fixed valve segment which extend out from either side of the venous valve 118. In particular the vein segments extending out from the valve will be greater than about 3 cm below the aggar and greater than about 2 cm above the valve commissures, preferably greater than about 5 cm in either direction.

Figures 12, 13:
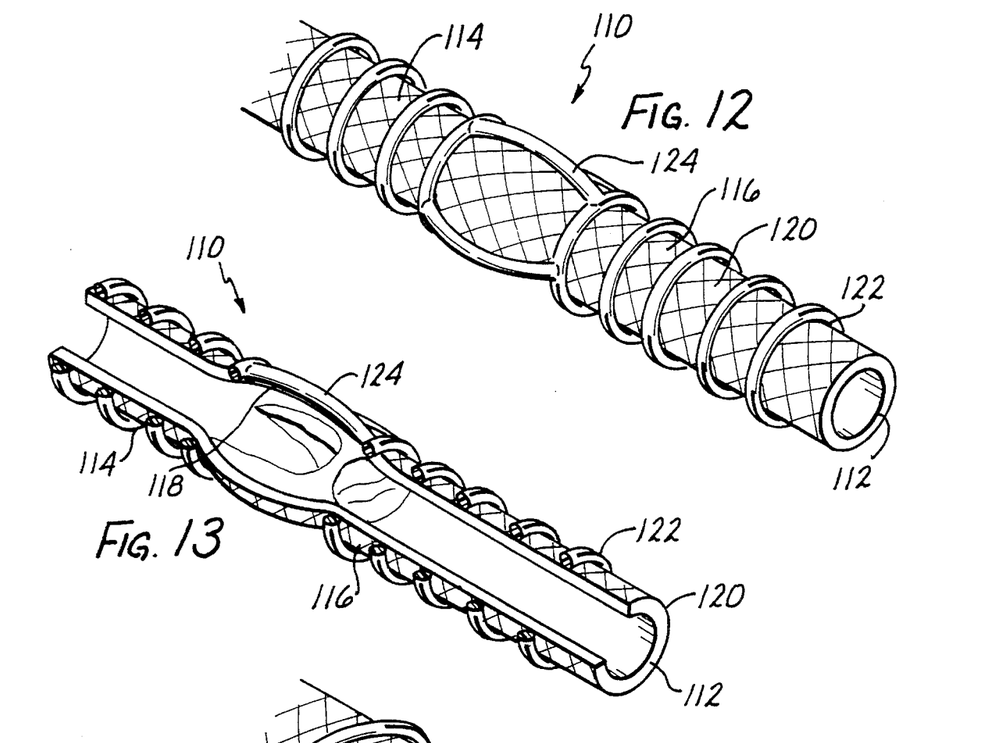
FIG. 12 is a prospective side view of a biological valvular conduit prosthesis in accordance with an embodiment of the invention.
FIG. 13 is a cross-sectional view of the valvular conduit prosthesis of FIG. 12.
Figures 14, 15:
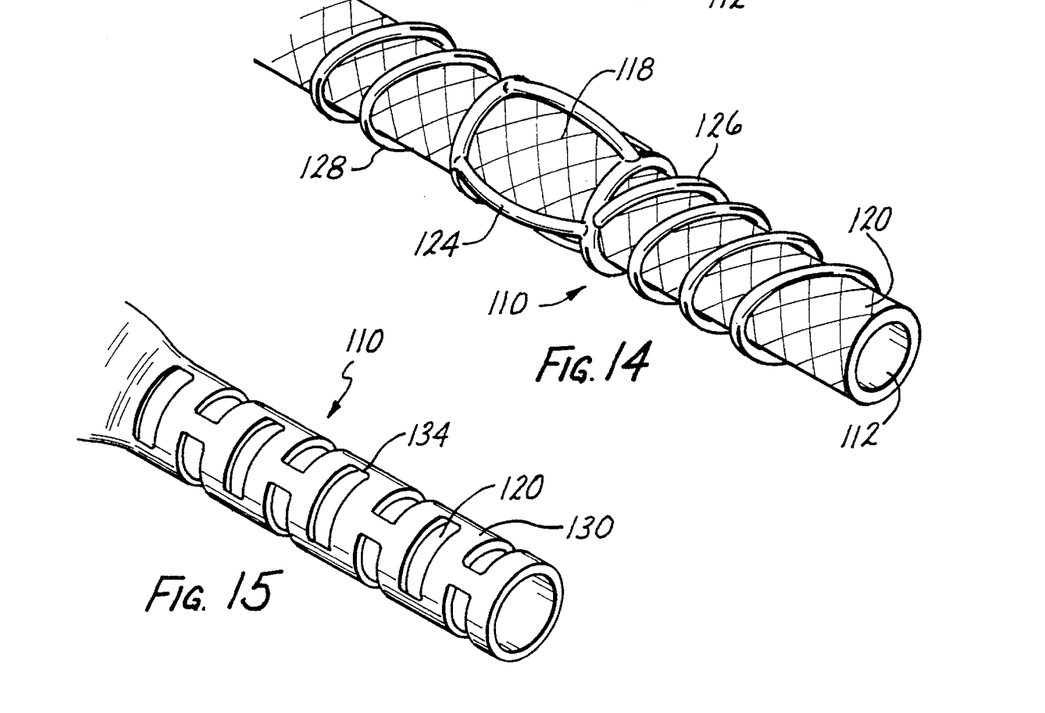
FIG. 14 is a side prospective view of a biological valvular conduit prosthesis in accordance with another embodiment of the invention.
FIG. 15 is a side prospective view of a biological valvular conduit prosthesis in accordance with a further embodiment.

The fixed vein portions 114 and 116 may be supported or reinforced to reduce possible collapse of such segments 114 and 116 during and after implantation. The biological vein segment 112, and in particular the portions 114 and 116, as seen in FIGS. 12 through 14 is supported by a cloth tube 120 wrapped either about the entire segment 112, or each of the individual portions 114. If the tube 120 encapsulates the entire vein segment 112, then it is dimensioned in the region of the valve 118 to allow dilation of the valve sinus.

The cloth tube 120 may be formed from Dacron, polytetrafluoroethylene, or other suitable biologically compatible materials. Tube 120 is generally constructed by wrapping a cloth about the biological vein segment 112 or individual portions 114 and 116. The valvular conduit 110 is further provided with a support cage 124 of similar construction and design to support cage 48 or 100 described above for the venous valvular replacement prosthesis 10. Additional support may be provided by fixing one or more individual reinforcing rings 122 about the prosthesis 110.

Other embodiments of the valvular conduit prosthesis are seen generally in FIGS. 14 and 15. All of the elements of the valvular conduit prosthesis seen in FIGS. 14 and 15 are the same as that described for the prosthesis 110 shown in FIGS. 12 and 13, except for the reinforcing rings 112. In the embodiment shown in FIG. 14, the individual reinforcing rings 112 are replaced by single spiral reinforcing members 126 and 128 positioned at opposite sides of the venous valve 118. The valvular conduit prosthesis 110 includes the cage 124.

The embodiment illustrated in FIG. 15 is a further variation in which the individual reinforcing rings 112 are replaced by single support members 130 and 132 positioned at opposite sides of the venous valve 118. These support members 130 and 132 are essentially conduits formed with a plurality of cutaways 134. Cutaways 134 are generally rectangular in shape and arranged in alternating off center rows. This arrangement provides the support members 130 and 132 with greater flexibility than would be obtained with a solid tubular member. Other possible configurations for the supporting of the segments 114 and 116 would be apparent to those skilled in the art.

The biological valvular conduit prosthesis 110 may be used anywhere a valve is required in the circulatory system. For example, this prosthesis 110 may be inserted into the patient's vein to bypass a defective venous valve in lieu of interposing the described venous valvular prothesis 10 in a patient's vein. The valvular conduit prosthesis 110 may also be used to reconstruct the pulmonary artery during the correction of various types of congenital birth defects of the right ventricular outflow tract. Examples of such defects include truncus arteriosus, pulmonary atresia and pulmonary stenosis.

Figure 16A:
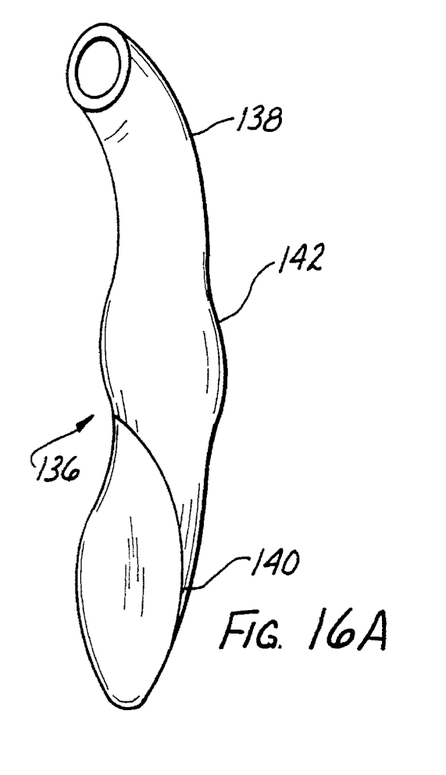
FIGS. 16A–C are illustrations of a modified valvular conduit prosthesis used for repair of truncus arteriosus.
Figure 16B:
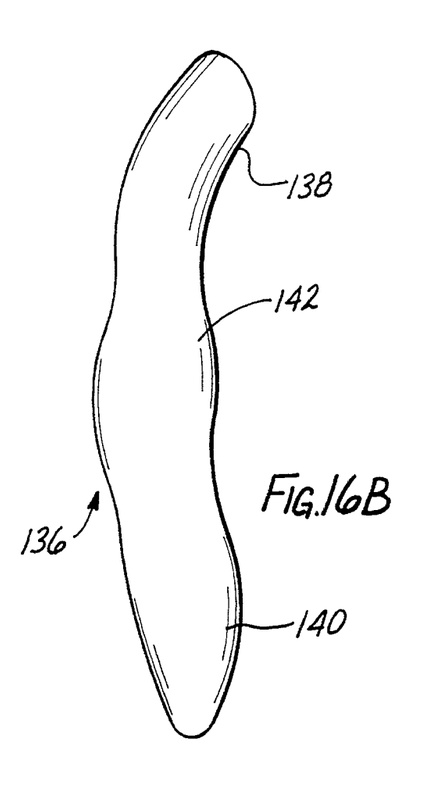
Figure 16C:
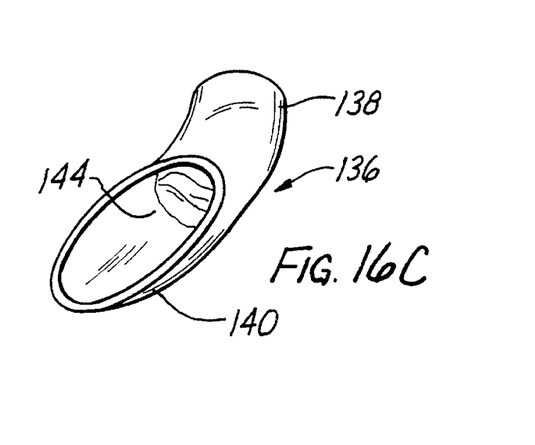

In using the biological valvular conduit prosthesis 110 in the reconstruction of the pulmonary artery, one or both of the vein segments at either side of the valve may be modified. An example of one particular type of modification is seen generally at 136 in FIGS. 16A–C. In this embodiment, a valvular conduit prothesis 136, prepared as described above, is formed with two segments 138 and 140 extending out from either side of the venous valve 142. These segments are formed by retaining an extended portion of the valve segment at either side of the valve after the fixation process. One of these segments 138 remains essentially unaltered after fixation and retained as a tubular body. The other segment 140 is cut lengthwise to form two portions. The cut is brought to within about two to about five centimeters of the valve. One of the portions is removed leaving only remaining portion to define a flap-like extension.

Valvular conduit prosthesis 136 has particular utilization in the reconstruction of the pulmonary artery in individuals suffering from truncus arteriosus. Truncus arteriosus is a congenital defect where a single artery arises from the heart in lieu of two separate arteries, the pulmonary and aortic. The artery communicates with both the left and right ventricles. A spatial defect is normally present with this defect. Blood entering the right ventricle, which normally passes to the lungs via the pulmonary artery, will pass through this defect directly into the left ventricle. Blood will also pass out of the right ventricle via the enlarged artery and travel through both the pulmonary and aortic segments. The result is the passage of unoxygenated blood to the aortic segment from the right ventricle.

Figures 17A, 17B, 17C:
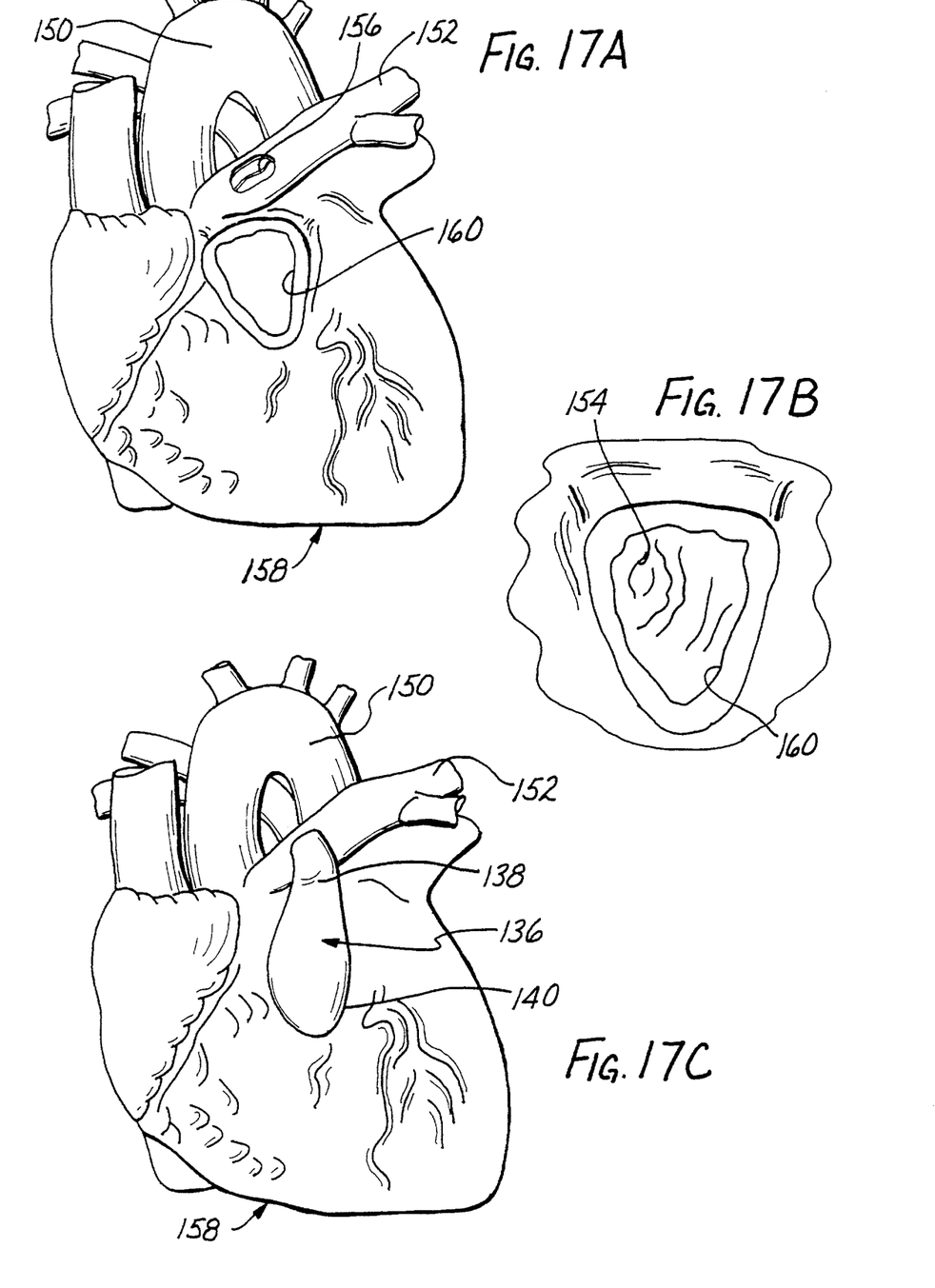
FIGS. 17A–C are illustrations of the surgical correction of truncus arteriosus using the valvular prosthesis illustrated in FIGS. 16A–C.

The reconstruction of a heart having this congenital defect will now be described with reference to FIGS. 17A–C. The first step typically involves surgically dividing the large single artery into the two individual aortic and pulmonary arteries, as seen in FIG. 17A at 150 and 152. Next a patch is sutured over the ventricular septal defect, typically a pericardial patch, seen at 154 in FIG. 17B. The aortic segment is also sealed with a patch, again typically a pericardial patch, seen at 156 in FIG. 17A. A connection between the right ventricle 158 and the pulmonary artery segment 152 is provided using the valvular conduit prosthesis 136. An opening 160 is made in the heart wall defining the right ventricle 158. The flap-like segment 140 of the valvular conduit prosthesis 136 is sutured to the right ventricle about this opening 160.

The prosthesis 136 may also include the various supporting elements described above for supporting the vein segments of the valvular conduit prosthesis 110. A plurality of rings may be positioned about the segment 138 in a manner similar to that illustrated and discussed for the conduit prosthesis embodiment of FIGS. 12 and 13, or a single spiral may be positioned about segment 138 as shown for the embodiment of FIG. 14 or a supporting member as shown in the embodiment of FIG. 15 may be positioned about the segment 138. The valve itself may also be supported as described for the valve of the conduit prosthesis 110. For example, a cage, similar to cage 124, may be positioned about the valve portion of the prosthesis 136. Preferably segment 140 is covered with fabric to provide support for the sutures.

While the preferred embodiments have been described, various modifications and substitutions may be made thereto without departing from the scope of the invention. Accordingly, it is to be understood that the invention has been described by way of illustration and not limitation.

What is claimed is:

1. A biological valvular prosthesis comprising:
   a chemically fixed conduit derived from a harvested vein segment bearing at least one integrally formed venous valve, said venous valve having at least one valve leaflet, wherein said venous valve is chemically fixed while retaining said valve leaflet in a substantially open position; and
   a restriction means positioned about said conduit at either side of said venous for restricting said venous valve from expanding outwardly, wherein said restriction means includes first and second rings positioned at opposite sides of said venous valve, with said rings being connected by one or more struts.

2. The biological valvular prosthesis of claim 1 wherein said at least one venous valve is chemically fixed while being retained in at least about seventy percent of its open position.

3. The biological valvular prosthesis of claim 1 wherein said at least one venous valve is chemically fixed to remain open at forward blood flow rates of greater than at least about one hundred milliliters/minute.

4. The biological valvular prosthesis of claim 2 wherein said at least one venous valve is chemically fixed to remain open at forward blood flow rates of greater than at least about one hundred milliliters/minute.

5. The biological valvular prosthesis of claim 3 wherein said at least one venous valve is chemically fixed to closed under back flow pressures of at least 0.1 mm Hg.

6. A biological valvular prosthesis comprising:
   a chemically fixed conduit derived from a harvested vein segment bearing at least one integrally formed venous valve, said venous valve having at least one valve leaflet, wherein said venous valve is chemically fixed while retaining said valve leaflet in a substantially closed position; and
   a restriction means positioned about said conduit at either side of said venous valve for restricting said venous valve from expanding outwardly, wherein said restriction means includes first and second rings positioned at opposite sides of said venous valve, with said rings being connected by one or more struts.

7. The biological valvular prosthesis of claim 6 wherein said at least one venous valve is chemically fixed to remain open at forward blood flow rates of greater than at least about one hundred milliliters/minute.

8. The biological valvular prosthesis of claim 7 wherein said at least one venous valve is chemically fixed to remain open at forward blood flow rates of greater than at least about one hundred milliliters/minute.

9. The biological valvular prosthesis of claim 8 wherein said at least one venous valve is chemically fixed to closed under back flow pressures of at least 0.1 mm Hg.

10. A biological valvular prosthesis comprising:
    a chemically fixed conduit derived from a harvested vein segment bearing at least one venous valve, wherein said venous valve is chemically fixed while being retained in the open position, said conduit including means positioned about said conduit for restricting said venous valve from expanding outwardly and protecting said venous valve from compression, wherein said means for restricting includes first and second rings positioned at opposite sides of said venous valve, with said rings being connected by one or more struts.

11. The biological valvular prosthesis of claim 10 wherein said at least one venous valve is chemically fixed while being retained in at least about seventy percent of its open position.

12. The biological valvular prosthesis of claim 10 wherein said at least one venous valve is chemically fixed to remain open at forward blood flow rates of greater than at least about one hundred milliliters/minute.

13. The biological valvular prosthesis of claim 11 wherein said at least one venous valve is chemically fixed to remain open at forward blood flow rates of greater than at least about one hundred milliliters/minute.

14. The biological valvular prosthesis of claim 12 wherein said at least one venous valve is chemically fixed to closed under back flow pressures of at least 0.1 mm Hg.

* * * * *